United States Patent [19]

Sih

[11] Patent Number: 4,710,468

[45] Date of Patent: * Dec. 1, 1987

[54] PROCESS FOR PREPARING L-CARNITINE AND CHEMICAL INTERMEDIATES EMPLOYED THEREIN

[75] Inventor: Charles J. Sih, Madison, Wis.

[73] Assignee: Sigma-Tau Industrie Pharmaceutiche Riunite S.p.A., Rome, Italy

[*] Notice: The portion of the term of this patent subsequent to Feb. 10, 2004 has been disclaimed.

[21] Appl. No.: 580,439

[22] Filed: Feb. 15, 1984

Related U.S. Application Data

[63] Continuation-in-part of Ser. No. 544,957, Oct. 24, 1983, which is a continuation-in-part of Ser. No. 447,171, Dec. 6, 1982, Pat. No. 4,642,290.

[51] Int. Cl.$^4$ .......................... C12P 7/62; C12P 7/52
[52] U.S. Cl. .................................... 435/135; 435/141
[58] Field of Search ............... 435/128, 135, 141, 280, 435/942

[56] References Cited

U.S. PATENT DOCUMENTS

| | | | |
|---|---|---|---|
| 3,823,069 | 7/1974 | Miyaki | 435/280 |
| 3,925,156 | 12/1975 | Chang et al. | 435/135 |
| 4,211,846 | 7/1980 | Lafferty | 435/829 X |
| 4,371,618 | 2/1983 | Cavazza | 435/128 |

FOREIGN PATENT DOCUMENTS

| | | | |
|---|---|---|---|
| 2268787 | 11/1975 | France . | |
| 0118438 | 9/1980 | Japan | 435/141 |
| 0111691 | 7/1983 | Japan | 435/141 |
| 0155094 | 9/1983 | Japan | 435/135 |

OTHER PUBLICATIONS

Nakamura et al, Tetrahedron Letters, vol. 25, No. 36, (1984), pp. 3979-3982.
Fuganti et al, Tetrahedron Letters, vol. 26, No. 1, (1985), pp. 101-104.
Seebach et al, Angew. Chem. Int. Ed. Engl., vol. 23, (1984), No. 2, pp. 151-152.
Morrison et al, Organic Chemistry, Third Edition, Boston, Allyn and Bacon, Inc., 1973, p. 1089.
Chemical Abstracts, vol. 84, 1976, Abstract No. 59999, Tenud.
Mori, Tetrahedron, vol. 37, (1981), pp. 1341-1342.
Limieux et al, Can. J. Chem., vol. 29, (1951), pp. 678-690.
Schweizer et al, Pro. Nat. Acad. Sci., 67:2, (1970), pp. 660-666.
Kuhn et al, Euro. J. Biochem., 24, (1972), pp. 492-497.
Block et al, Acta Chemica Scandinavica, B, 37(4), 1983, pp. 341-344.
Chemical Abstracts, vol. 99, 1983, Abstract No. 103632f, Zhou et al. .
S. Deol et al., Aust. J. Chem., (1976), 29, 2459.
Chem. Abstr., 78, (1973), 147382v.
Chem. Abstr., 75, (1971), 19716h.
Frater, Helvetica Chimica Acta, vol. 62, (1979), pp. 2829-2832.
Hirama et al, J. Am. Chem. Soc., vol. 104, (1982), pp. 4251-4253.
Zhou et al, J. Am. Chem. Soc., vol. 105, pp. 5925-5926, (1983).
Hirama et al, J. Chem. Soc., Chem. Commun., (1983), pp. 599-600.
Lynen, "Yeast Fatty Acid Synthase", In: Methods in Enzymology, vol. 14, (1969), pp. 17-33.
Enzyme Nomenclature, Elsevier Scientific Publishing, Amsterdam, (1973), pp. 46-47.
Barman, Enzyme Handbook, vol. 1, Springer-Verlag, New York, (1969), p. 55.

*Primary Examiner*—Robert J. Warden
*Assistant Examiner*—Randall E. Deck
*Attorney, Agent, or Firm*—Isaksen, Lathrop, Esch, Hart & Clark

[57] ABSTRACT

A process for preparing L-carnitine which comprises exposing γ-substituted acetoacetic acid esters or amides to the fermentative enzymatic action of a microorganism which elaborates L-β-hydroxyacyl CoA dehydrogenase [EC 1.1.1.35], recovering the resulting, optically active corresponding γ-substituted-β-hydroxybutyric acid derivative and converting said derivative to L-carnitine. An improvement in the process is also disclosed which comprises reacting a 4-chloro-3(R)-hydroxybutyrate with sodium iodide or bromide to produce the corresponding 4-iodo- or 4-bromo-3(R)-hydroxybutyrate, converting the 4-iodo- or 4-bromo-3(R)-hydroxybutyrate to the trimethylamino-3(R)-hydroxybutyrate salt, then converting the trimethylamino-3(R)-hydroxybutyrate salt into L-carnitine. Novel chemical intermediates prepared in the processes are also disclosed.

3 Claims, No Drawings

PROCESS FOR PREPARING L-CARNITINE AND CHEMICAL INTERMEDIATES EMPLOYED THEREIN

CROSS REFERENCE TO RELATED APPLICATIONS

This application is a continuation-in-part of the earlier co-pending application Ser. No. 544,957, filed Oct. 24, 1983, itself a continuation-in-part of the co-pending application Ser. No. 447,171 filed Dec. 6, 1982, now U.S. Pat. No. 4,642,290.

FIELD OF THE INVENTION

The present invention relates to processes for producing L-carnitine. Specifically, it relates to a process for microbiologically reducing γ-substituted-acetoacetic esters or amides into their respective R-β-hydroxy-γ-substituted-butyric acid derivatives, which derivatives can be readily converted into L-carnitine chloride. It also relates to novel chemical intermediates employed in the process.

BACKGROUND OF THE INVENTION

As is well known, carnitine (β-hydroxy-γ-trimethylamino butyric acid) contains a center of asymmetry and, therefore, carnitine exists in two stereoisomeric forms, the D and the L forms.

L-carnitine is normally present in the body where it functions to carry activated long-chain free fatty acids through the mitochondrial membrane. Since the mitochondrial membrane is impermeable to acyl CoA derivatives, long-chain free fatty acids can enter only when esterification with L-carnitine has taken place. The carrier function of L-carnitine is exerted both in transporting active long-chain fatty acids from the sites of their bio-synthesis, for the example the microsomes, to the mitochondria where they are oxidized, and by transporting acetyl CoA from the mitochondria, wherein it is formed, to the extramitochondrial sites where the synthesis of long-chain fatty acids occurs, e.g., in the microsomes wherein acetyl CoA can be utilized for synthesizing cholesterol and fatty acids.

While it has been established that the laevorotatory isomer (L-carnitine) exclusively is the biologic form (D-carnitine has never been detected so far in mammalian tissues), the D,L-carnitine racemate has been used for a number of years for a variety of indications. For example, D,L-carnitine is sold in Europe as an appetite stimulant, and it has been reported that the material has an effect on the growth rate of children; see e.g., Borniche et al., *Clinica Chemica Acta* (1960) 5, 171–176, and Alexander et al., "Protides in the Biological Fluids," 6th Colloquium, Bruges, 1958, 306–310. U.S. Pat. No. 3,830,931 describes improvements in myocardial contractility and systolic rhythm in congestive heart failure which can often be obtained through administration of D,L-carnitine. U.S. Pat. No. 3,968,241 describes the use of D,L-carnitine in cardiac arrythmias. U.S. Pat. No. 3,810,994 discloses the use of D,L-carnitine in the treatment of obesity.

Recently, however, there has been an increasing emphasis on the importance of utilizing exclusively the carnitine laevorotatory isomer for at least some therapeutic applications. It has, in fact, been shown that D-carnitine is a competitive inhibitor of carnitine-linked enzymes such as carnitine acetyl transferase (CAT) and carnitine palmityl transferase (PTC). Moreover, recent evidence suggests that D-carnitine can deplete the L-carnitine level of heart tissue. Consequently, it is essential that L-carnitine exclusively be administered to patients under medical treatment for heart diseases or lowering of blood lipids.

Several processes have been proposed for producing carnitine on an industrial scale. The chemical synthesis of carnitine unavoidably leads, however, to a racemic mixture of the D and L isomers. Consequently, resolution methods have to be employed to obtain the separate optical anitipodes from the racemate.

A typical resolution method wherein D,L-carnitinamide hydrochloride is used as the starting compound for resolution is disclosed in Belgian Pat. No. 660039. Such process comprises the use of D-camphoric acid for producing the D-camphorate of D,L-carnitinamide. An alcoholic solution of this compound is subjected to fractional crystallization so as to give the L-isomer as the first fraction to precipitate from the solution.

In order to form the D-camphorate of D,L-carnitinamide, it is first necessary to form the ammonium salt of D-camphoric acid with ammonia; the ammonium D-camphorate that is formed is then converted to silver D-camphorate by the action of silver nitrate. Since the carnitinamide is in the hydrochloride salt form, the formation of this silver salt is essential in order to eliminate the chloride ion. Such a process is, therefore, very expensive (because of the imperative use of the silver compound) and difficult to carry out industrially in that the various steps of the process have to be carried out away from the light in order to avoid marked blackening of the reaction vessels, due to the large quantity of AgCl which is formed. The D-camphorate of D,L-carnitinamide may, in addition, be rendered impure by the presence of silver ions. Moreover, after the D-camphorate of L-carnitinamide has been crystallized out of the alcoholic solution, further steps are needed to eventually convert it into L-carnitine.

DESCRIPTION OF THE INVENTION

It is an object of this invention to produce L-carnitine chloride in good yield through a combination of microbiological and chemical processes.

An object of the present invention is to provide an improved process for synthesizing L-carnitine from readily available moderate cost raw materials.

Another object of the present invention is to disclose the preparation of novel, useful optically-active intermediates for the synthesis of L-carnitine and its salts or esters.

Another object of the present invention is to provide processes for preparing L-carnitine via the trimethylamine displacement of the halo group of a 4-halo-3(R)-hydroxybutyrate.

Still another object of the present invention is to provide a process for producing 4-iodo or 4-bromo-3(R)-hydroxybutyrates from 4-chloro-3(R)-hydroxybutyrates.

These and other objects of the invention will become more apparent as the description thereof proceeds. The advantages of the present invention will be apparent to those skilled in the art from the following detailed description.

That the β-keto function in the 3-position in the γ-substituted-acetoacetic acid derivatives can be reduced by hydrogenation over Pt/C is known (e.g., U.S. Pat. No. 3,969,406). However, the hydroxy compound resulting from such method is racemic. In contrast, by employing the fermentative action of a microorganism in accordance with the process of the present invention, the hydrogenation of the oxo-function at the 3-position can be accomplished stereoselectively to yield the 3(R) or L epimeric configuration. This configuration is required for the conversion into the natural L-carnitine.

Broadly this invention comprises the use of the microbial oxido reductase enzyme, L-β-hydroxyacyl CoA dehydrogenase [EC 1.1.1.35], to catalyze stereoselective hydrogenation of γ-substituted acetoacetic acid derivatives having the formula

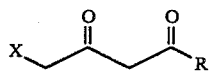

wherein X is selected from Cl, Br, I and OH, and R is a radical in straight chain, branched chain, or cyclic configuration selected from the class consisting of alkoxy radicals having from 1 to about 15 carbon atoms; alkylamino radicals having from about 5 to about 15 carbon atoms; cycloalkoxy radicals and cycloalkylamino radicals having from about 5 to about 12 carbon atoms; phenoxy and phenylalkoxy radicals having from 7 to about 14 carbon atoms; and phenylamino and phenylalkylamino radicals having the formula

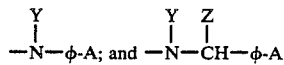

where Y and Z are selected from H, an alkyl group having from 1 to about 8 carbon atoms, phenyl, or benzyl and A is selected from H, CH₃, Cl, and Br.

It will be obvious to those skilled in the art that for the purposes of this invention the substituent designated as R in the above acetoacetic-system can vary widely. Thus, it can be a saturated or unsaturated, or a substituted or unsubstituted, ester or amide grouping, and it can be aliphatic, cyclic, or aromatic in nature, or can comprise any mixture thereof so long as the particular R group selected permits the compound to be hydrogenated by the enzyme.

It has been found that any microorganism which produces the desired enzyme is capable of functioning to catalyze the stereoselective reduction. Particularly suitable are those microorganisms of the class Ascomycetes and the order Endomycetales, Mucorales, Moniliales, and Eurotialis.

To prepare optically-active 4-chloro-3(R)-hydroxybutyrate esters containing from one to four carbon atoms in the ester group, it is necessary to use purified L-β-hydroxyacyl CoA dehydrogenase [EC 1 1.1.35] such as that from porcine heart, because most intact microorganisms of the sort referred to above possess interfering oxido-reductases of opposing configuration. As a consequence of the action of the interfering oxido-reductases, microbial reduction of 4-chloroacetoacetic esters having from one to four carbons in the ester group produces 4-chloro-3-hydroxybutyrates of unsatisfactory optical purities. On the other hand, it is possible to use mutants of such microorganisms that lack the interfering oxido-reductase (e.g., lacks the β-keto-reductase componet of fatty acid synthetase) enzyme for the preparation of 4-chloro-3(R)-hydroxybutyrate esters containing from one to four carbon atoms. Especially suitable for this purpose are the mutants of *Saccharomyces cerevisiae* that have been given the American Type Culture Collection designations ATCC 26403 and ATCC 26405.

The optically-active γ-substituted-R-β-hydroxybutyric acid derivatives may then be reacted with trimethylamine to yield the corresponding γ-trimethylammonium-R-β-hydroxybutyric acid derivative, which can be readily converted into L-carnitine by treatment with aqueous acids. The following is a schematic of the reaction steps of this process.

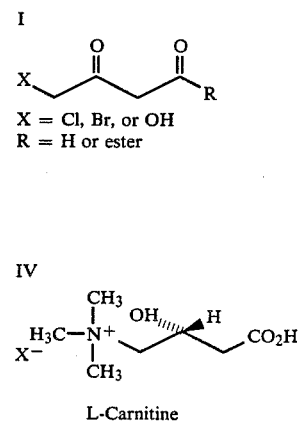

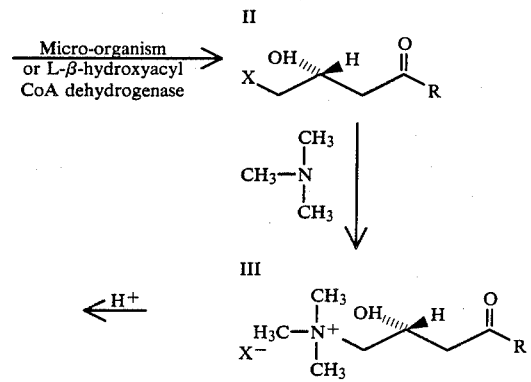

Although the reaction of trimethylamine with the 4-chloro-3(R)-hydroxybutyrate (II) proceeds in satisfactory yields on small scales (1g), the yield of III drops significantly on a larger scale (>100 g). The present invention also relates to an improved process which comprises first converting 4-chloro-3(R)-hydroxybutyrate ester containing 1 to 10 carbon atoms to the corresponding 4-iodo or 4-bromo-3(R)-hydroxybutyrates (Va and vb). The iodohydrin (Va), or the bromohydrin (Vb) may be reaced smoothly with trimethylamaine at room temperature to yield VI which is readily converted to L-carnitine according to the following reaction sequence:

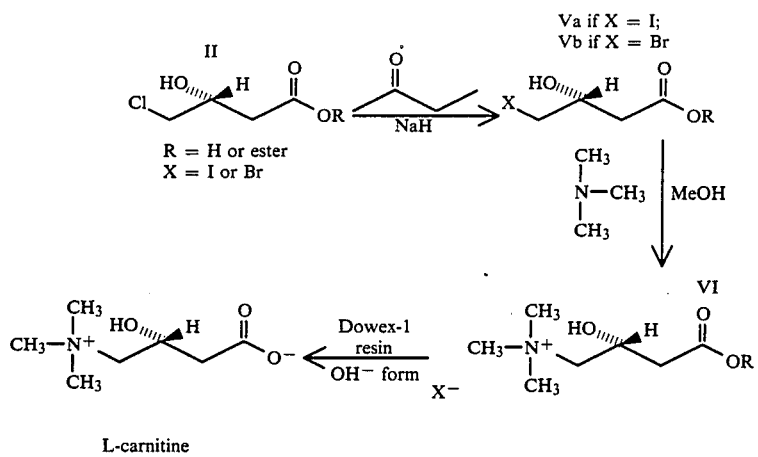

The foregoing process as exemplified by the equation is subject to numerous variations. Regardless of which form is then made available, the ester is reacted with sodium iodide in a suitable solvent such as 2-butanone, acetone, butanol, etc. The principal reaction desired at this point in the reaction with sodium iodine is a displacement reaction which forms the iodohydrin V without disturbing the chiral center on the adjacent carbon atom. For this reaction at least enough sodium iodide or bromide is required to displace all chloride from II. Generally speaking, a slight excess of sodium iodide or bromide is used.

The reaction of V with trimethylamine can be carried out at mild temperature (e.g., 25° C.) [See S. G. Boots and M. R. Boots, J. Pharm. Sci. (1975) 64, 1262], in a variety of solvents such as methanol or ethanol containing an excess of trimethylamine. It is noteworthy that depending on the alcoholic solvent used, there is ester exchange taking place. For example, when methanol is used as solvent, L-carnitine methyl ester is obtained in the reaction. This exchange reaction is advantageous because it is known that L-carnitine methyl ester can be transformed directly to the free base form of L-carnitine by passing through an ion-exchange column (OH−) [see E. Strack and J. Lorenz, J. Physiol. Chem. (1966) 344, 276].

It can be seen from the description of the foregoing processes that a number of new and highly useful optically-active intermediates are formed. Especially useful are the 4-iodo-and 4-bromo-3(R)-hydroxybutyric acid alkyl esters where the alkyl groups have from one to ten carbon atoms each.

Microorganisms which have the desired dehydrogenase activity are well known in the microbiological art and any of such microorganisms can be employed in conducting the process of the present invention [See, K. Kieslich, "Microbial Transformations of Non-Steroid Cyclic Compounds" (Georg Thieme Publishers, Stuttgart, 1976)] with any of the genera of microorganisms specifically described herein being particularly applicable. Readily available and inexpensive microorganisms of the genera Saccharomyces, e.g., brewer's yeast, baker's yeast, and winemaker's yeast (Saccharomyces vini) have been found to produce the L-β-hydroxylacyl CoA dehydrogenase [EC 1.1.1.35] and to be eminently advantageous in carrying out the process of the invention. The enzyme is described by S. J. Wakil and E. M. Barnes, Jr. in Comprehensive Biochemistry (1971) 185, 57–104.

The 4-substituted-acetoacetic substrate can be incorporated in a nutrient medium of standard composition in which such organisms are cultivated, and the usual conditions of fermentation can then be employed to effect the reductive transformation. Alternatively, the active principle can be removed from the growing culture of the microorganism, for instance by lysis of the cells to release the enzymes, or by suspension of the resting cells in a fresh aqueous system. In any of these techniques the B-keto function will be selectively reduced, so long as the active enzyme elaborated by the microorganisms is present in the medium. Of course, the temperature, time, and pressure conditions under which the contact of the 4-substituted-acetoacetic derivative with the reductive enzyme is carried out are interdependent as will be apparent to those skilled in the art. For instance, with gentle heating and at atmospheric pressure the time required to effect the reductive conversion will be less than if it progresses at room temperature under conditions otherwise the same. Of course, neither temperature, pressure, nor time should be so great that the substrate is degraded. Where a growing culture of the organism is being used, the process conditions should also be sufficiently gentle that the organism is not killed before it elaborates sufficient hydrolytic enzymes to permit the reaction to proceed. Generally, at atmospheric pressure, the temperature can range from about 10° C. to about 35° C., and the time from about 10 days on to about 12 hours.

In the following examples which are presented to illustrate this invention and are not to be construed as limiting the scope of the appended claims, the γ-halo acetoacetic acid derivative substrates to be subjected to microbiological reduction were prepared from diketene according to the general method of C. D. Hurd and H. L. Abernethy [J. Am. Chem. Soc. (1940) 62, 1147] for the γ-chloro-acetoacetic derivatives and F. Chick, N. T. M. Wilsmore [J. Chem. Soc., 1978 (1910)] for the γ-bromo-acetoacetic derivatives via the following reaction sequence:

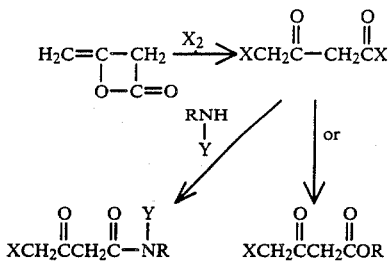

where
X=Cl or Br
Y=H or alkyl
R=as defined previously

Alternatively, if desired, the γ-halo acetoacetic acid derivatives can be prepared from γ-halo acetic esters via a conventional Grignard reaction. For example γ-chloro acetoacetic octyl ester was readily prepared by refluxing octyl-2-chloroacetate with two equivalents of magnesium in ether for 48 hours. After removal of the solvent, the acetoacetic octyl ester was recovered in about 70% yield.

γ-hydroxy acetoacetic acid derivatives were prepared from their corresponding γ-bromo acetoacetic acid derivatives by stirring in a dioxane-water (1:1) solution containing $CaCO_3$ at 25° C. for 12 hours.

Each of the products produced in accordance with the following examples was identified as to structure through the use of nuclear magnetic resonance (nmr), infrared spectra, and by thin layer chromatographic mobilities. The optical purity and the absolute configuration of the products were established by their conversion into L-carnitine as well as by conversion into their esters which are readily analyzed by nmr spectrometry, and optical rotation.

EXAMPLE 1 (YEASTS)

(+)4-chloro-3(R)-hydroxybutyric acid octyl ester was prepared as follows:

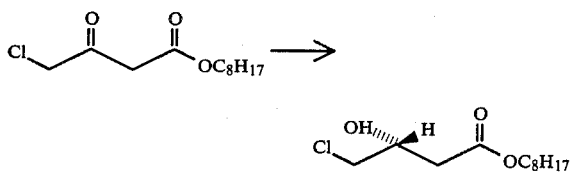

A. Fermentation. Surface growth from a one week old agar slant of *Candida keyfr.* NRRL Y-329, grown on agar of the following composition:

| | Gms |
|---|---|
| Agar | 20 |
| Glucose | 10 |
| Yeast extract | 2.5 |
| $K_2HPO_4$ | 1 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flask (F-1 stage) containing 50 ml of the following medium (Vogel's medium):

| | Gms |
|---|---|
| Yeast extract | 5 |
| Casamino acids | 5 |
| Dextrose | 40 |
| $Na_3$—citrate-5½ $H_2O$ | 3 |
| $KH_2PO_4$ | 5 |
| $NH_4NO_3$ | 2 |
| $CaCl_2$ $2H_2O$ | 0.1 |
| $MgSO_4$ $7H_2O$ | 0.2 |
| Trace element solution | 0.1 ml |
| Distilled water, q.s. 1 liter | |
| pH 5.6 (sterilized for 15 min at 30 p.s.i.) | |

| Trace element solution | Gm/100 ml |
|---|---|
| Citric acid-1$H_2O$ | 5 |
| $ZnSO_4$ $7H_2O$ | 7 |
| $Fe(NH_4)_2(SO_4)_2$ $6H_2O$ | 1 |
| $CuSO_4$ $5H_2O$ | 0.25 |
| $MnSO_4$ $1H_2O$ | 0.05 |
| $H_3BO_3$ | 0.05 |
| $NaH_2MoO_4$ $2H_2O$ | 0.05 |

The flask was incubated at 25° C. on a rotary shaker (250 cycles/min- 2" radius) for 24 hours, after which a 10% by volume transfer was made to another 250 ml Erlenmeyer flask (F-2 stage) containing 50 ml of Vogel's medium. After 24 hours of incubation on a rotary shaker, 150 mg of γ-chloroacetoacetic acid octyl ester in 0.1 ml of 10% Tween 80 was added. The F-2 stage flask was then incubated for an additional 24 hours under the conditions used in the incubation of the F-1 stage flasks.

B. Isolation. Twenty-four hours after the addition of the γ-chloroacetoacetic acid octyl ester, the cells were removed by centrifugation. The supernatant was exhaustively extracted with 50 ml of ethyl acetate three times. The ethyl acetate was dried over $Na_2SO_4$ and evaporated to afford an oily residue (186 mg). The residue was dissolved in 0.5 ml of the mobile phase and added onto a column (1×25 cm) of silica gel (MN-kieselgel 60). The column was eluted with Skelly B:ethyl acetate (8:1) and 14 ml fractions were collected. Fractions 6 and 7 containing the desired product were pooled and concentrated to dryness yielding 120 mg of crystalline residue. Recrystallization from ethyl acetate-hexane afforded 107 mg of 4-chloro-3(R)-hydroxybutyric acid octyl ester, $[\alpha]^{23}+13.3°$ (c 4.45) ($CHCl_3$); pmr (δ $CDCl_3$) 0.88 [3H, tr. distortional, $CH_3$-$(CH_2)_n$-]; 1.28 [10H, s, -$(CH_2)_5$]; 1.65

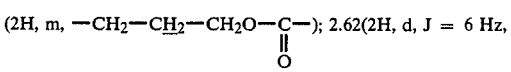

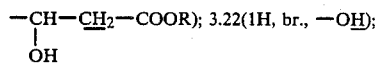

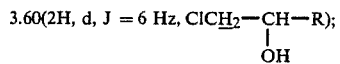

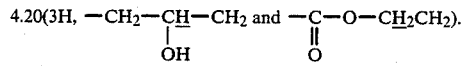

Anal. Calcd for $C_{12}H_{23}O_3Cl$: C, 57.47; H, 9.25. Found: C, 57.52; H, 9.07. [TLC $R_f$-0.5, Brinkmann silica gel plate, 0.25 cm EM; Skelly B:ethyl acetate (5:1).]

EXAMPLE 2

Resting Cells. One hundred grams of commercial fresh baker's yeast *Saccharomyces cerevisiae* (Red Star) was suspended in 250 ml of tap water to which was added 10 g of sucrose and 3.6 g of γ-chloroacetoacetic octyl ester. After the contents were incubated at 25° C. on a rotary shaker (250 cycles/minute- 2" radius) for 24 hours, an additional 10 q of sucrose was added to the flask and the reaction was allowed to proceed for another 24 hours. The cells were then removed by filtration through a pad of celite. The cells were washed with water and ethyl acetate. The washings were combined with the filtrate and exhaustively extracted with ethyl acetate. The ethyl acetate layer was dried over MgSO4 and evaporated to give an oily residue, which was chromatographed over a silica gel column to yield 2.52 g of 4-chloro-3(R)-hydroxybutyric acid octyl ester, as a low melting solid; $[\alpha]^{23} + 13.2°$ (c, 4.0,CHCl3).

EXAMPLE 3

(+)4-Chloro-3(R)hydroxybutyric acid benzyl ester was prepared as follows:

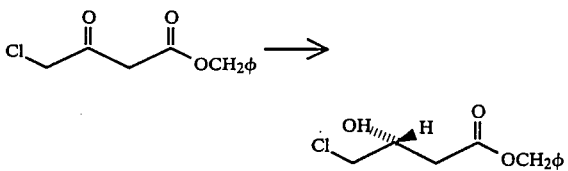

A. Fermentation. Surface growth from a one week old agar slant of *Gliocladium virens* ATCC 13362, grown on agar of the following composition:

|  | Gms |
| --- | --- |
| Malt extract | 20 |
| Glucose | 20 |
| Peptone | 1 |
| Agar | 20 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flask (F-1 stage) containing 50 ml of the following medium (Soybean dextrose medium):

| Soybean meal | 5 g |
| --- | --- |
| Dextrose | 20 g |
| NaCl | 5 g |
| KH2HPO4 | 5 g |
| Yeast | 5 g |
| Water | 1 l |
| pH adjusted to 7.0 | |
| Autoclave at 15 p.s.i. for 15 minutes | |

The flask was incubated at 25° C. on a rotary shaker (250 cycles/min- 2" radius) for 24 hours, after which a 10% by volume transfer was made to another 250 ml Erlenmeyer flask (F-2 stage) containing 50 ml of soybean dextrose medium. After 24 hours of incubation on a rotary shaker, 150 mg of γ-chloroacetoacetic benzyl ester in 0.1 ml of 10% Tween 80 was added. The F-2 stage flask was then incubated for an additional 24 hours under the conditions used in the incubation of the F-1 stage flasks.

B. Isolation. Twenty-four hours after the addition of the γ-chloroacetoacetic benzyl ester, the mycelia were removed by filtration. The filtrate was exhaustively extracted with 50 ml of ethyl acetate three times. The ethyl acetate layer was dried over MgSO4 and concentrated in vacuo to yield a residue (160 mg). The residue was chromatographed over a silica gel (MN-Kieselgel 60) column (1×25 cm). The column was eluted with Skelly B and ethyl acetate (10:1) and 12 ml fractions were collected. Fractions 11-16 containing the desired product were pooled and concentrated to dryness to afford 115 mg of 4-chloro-3(R)-hyroxybutyric acid benzyl ester, $[\alpha]_D^{23} + 8.7°$ (5.26; CHCl3); pmr (δCDCl3)2.65.

(2H, d, J = 6Hz, —CH—CH2COOR), 3.20(1H, br, —OH);
$\quad\quad\quad\quad\quad\quad\quad\quad\quad$ |
$\quad\quad\quad\quad\quad\quad\quad\quad\quad$ OH 3.54(2H, d, J = 6Hz, Cl—CH2CH);
$\quad\quad\quad\quad\quad\quad\quad\quad\quad\quad\quad$ |
$\quad\quad\quad\quad\quad\quad\quad\quad\quad\quad\quad$ OH 4.20(1H, m, —CH2—CH—CH2—),
$\quad\quad\quad\quad\quad\quad\quad\quad\quad$ |
$\quad\quad\quad\quad\quad\quad\quad\quad\quad$ OH 5.12(2H, s, —C—O—CH2C6H5);
$\quad\quad\quad\quad\quad\quad$ ||
$\quad\quad\quad\quad\quad\quad$ O 7.31(5H, s, five aromatic protons).

Anal. calcd. for C11H13O3Cl: C, 57.77; H, 5.73. Found: C, 57.64; H, 5.67. [TLC silica gel EM Brinkmann plate, 0.25 cm, Rf=0.43, Skelly B-ethyl acetate (5:1).]

EXAMPLE 4-23

The procedure of Example 1 was repeated with each of the organisms listed in Table 1 except that 4-chloroacetoacetic acid octyl ester was added at a concentration of 1 mg/ml. Conversion to the desired product (+)4-chloro-3(R)-hydroxybutyric acid octyl ester was obtained. The procedures of these examples were repeated by continuously adding the substrate to the yeast medium. The weight ratio substrate/yeast was about 1:1.5 with excellent conversion to the desired product.

EXAMPLES 24-48

The procedure of Example 3 was repeated with each of the organisms listed in Table 2 except that γ-chloroacetoacetic octyl ester (1 mg/ml) was used. Transformation to the desired compound (+)4-chloro-3(R)-hydroxybutyric acid octyl ester was obtained.

EXAMPLES 49-68

The procedure of Example 1 was repeated with each of the organisms listed in Table 1 except that γ-chloroacetoacetic acid benzyl ester (1 mg/ml) was used as the substrate. Conversion to the desired product (+)4-chloro-3(R)-hydroxybutyric acid benzyl ester was obtained.

EXAMPLES 69-93

The procedure of Example 3 was repeated with each of the organisms listed in Table 2 using γ-chloroacetoacetic acid benzyl ester (1 mg/ml) as substrate. Transformation to the desired compound (+)4-chloro-3(R)-hydroxybutyric acid benzyl ester was obtained.

EXAMPLE 94

(+)4-Chloro-3(R)-hydroxybutyric acid anilide was prepared in accordance with the procedure of Example 2 except that 4-chloroacetoacetanilide was used at a concentration of 1 mg/ml.

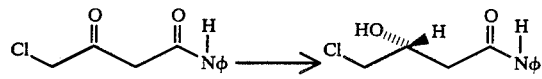

as the substrate for the conversion into the desired optically-active product, m.p.110°–111° C.; $[\alpha]^{23} = +17.5°$ (c, 3.0, CHCl$_3$); pmr

2.67 (2H, d, J=6 Hz, —HOHCH—$_2$—CONHR), 3.66 (2H, d, J=6 Hz, ClCH—$_2$CHOH—R), 4,43 (1H, m, —CH$_2$—CHOH—CH$_2$—), 7.03–7.44 (3H, m, aromatic protons, meta and para), 7.69 (2H, d, J=6 Hz, aromatic protons, ortho) 9.24

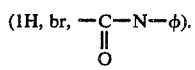

Anal. calcd for C$_{10}$H$_{12}$NO$_2$Cl: C, 56.21; H, 5.66. Found: C, 56.17; H, 5.47.

EXAMPLES 95–114

The procedure of Example 1 was repeated with each of the organisms listed in Table 1 except that 4-chloroacetoacetanilide was added at a concentration of 1 mg/ml. In all cases conversion to the desired product, (+)4-chloro-3(R)-hydroxybutyric acid anilide was obtained.

EXAMPLES 115–139

The procedure of Example 3 was repeated with the organisms listed in Table 2. γ-Chloroacetoacetanilide was introduced at a concentration of 1 mg/ml. In these cases, conversion to the desired (+)4-chloro-3(R)-hydroxybutyric acid anilide was achieved.

EXAMPLES 140–159

The procedure of Example 1 was repeated with the organisms listed in Table 1 except that γ-bromoacetoacetic acid octyl ester (1 mg/ml) was used as the substrate. Conversion to the desired product, (+)4-bromo-3(R)-hydroxybutyric acid octyl ester was obtained.

EXAMPLES 160–184

The procedure of Example 3 was repeated with the organisms listed in Table 2 except that γ-bromoacetoacetic acid octyl ester (1 mg/ml) was used. Conversion to the desired product, (+)4-bromo-3(R)-hydroxybutyric acid octyl ester was obtained.

EXAMPLES 185–204

The procedure of Example 1 was repeated with the organisms listed in Table 1 except that γ-bromoacetoacetic acid benzyl ester (1 mg/ml) was used as the substrate. Conversion to the desired product, (+)4-bromo-3(R)-hydroxybutyric acid benzyl ester was obtained.

EXAMPLES 205–229

The procedure of Example 3 was repeated with the organisms listed in Table 2 except that γ-bromoacetoacetic acid benzyl ester (1 mg/ml) was used. Conversion to the desired product, (+)4-bromo-3(R)-hydroxybutyric acid benzyl ester was obtained.

EXAMPLES 230–249

The procedure of Example 1 was repeated with the organisms listed in Table 1 except that γ-bromoacetanilide (1 mg/ml) was used as the substrate. Conversion to the desired (+)4-bromo-3(R)-hydroxybutyric acid anilide was obtained.

EXAMPLES 250–274

The procedure of Example 3 was repeated with the organisms listed in Table 2 except that γ-bromoacetanilide (1 mg/ml) was used as the substrate. Conversion to the desired (+)4-bromo-3(R)-hydroxybutyric acid anilide was obtained.

EXAMPLE 275–294

The procedure of Example 1 was repeated with the organisms listed in Table 1 except that γ-hydroxyacetoacetic octyl ester (1 mg/ml) was used as the substrate. Conversion to the desired 4-hydroxy-3(R)-hydroxybutyric acid octyl ester was obtained.

EXAMPLES 295–319

The procedure of Example 3 was repeated with the organisms listed in Table 2 except that γ-hydroxyacetoacetic octyl ester (1 mg/ml) was used as the substrate. Conversion to the desired 4-hydroxy-3(R)-hydroxybutyric acid octyl ester was obtained.

EXAMPLES 320–339

The procedure of Example 1 was repeated with the organisms listed in Table 1 except that γ-hydroxyacetoacetanilide (1 mg/ml) was used as the substrate. Conversion to the desired 4-hydroxy-3(R)-hydroxybutyric acid anilide was obtained.

EXAMPLES 340–364

The procedure of Example 3 was repeated with the organisms listed in Table 2 except that γ-hydroxyacetoacetanilide (1 mg/ml) was used as the substrate. Conversion to the desired 4-hydroxy-3(R)-hydroxybutyric acid anilide was obtained.

EXAMPLE 365

The procedure of Example 2 was repeated except 4-chloroacetoacetic pentyl ester (1 mg/ml) was used as the substrate. Conversion to the desired 4-hydroxy-3(R)-hydroxybutyric pentyl ester was obtained.

EXAMPLE 366

The procedure of Example 2 was repeated except 4-chloroacetoacetic hexyl ester (5 mg/ml) was used as the substrate. Conversion to the desired 4-chloro-3(R)-hydroxybutyric hexyl ester was obtained.

EXAMPLES 367

The procedure of Example 2 was repeated except 4-chloroacetoacetic heptyl ester (10 mg/ml) was used as the substrate. Conversion to the desired 4-chloro-3(R)-hydroxybutyric heptyl ester was obtained.

EXAMPLE 368

The procedure of Example 2 was repeated except 4-chloroacetoacetic decyl ester (10 mg/ml) was used as the substrate. Conversion to the desired 4-chloro-3(R)-hydroxybutyric decyl ester was obtained.

EXAMPLE 369

General procedure for the preparation of 4-chloro-3(R)-hydroxybutyrate esters containing 1–4 carbon atoms using mutants of Saccharomyces cerevisiae (ATCC 26403).

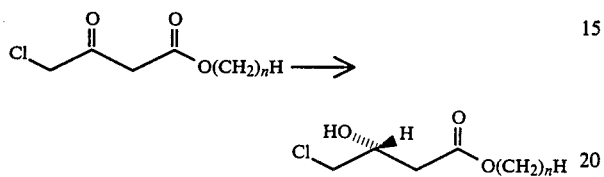

(A) Fermentation. Surface growth from a one week old agar slant of *Saccharomyces cerevisiae* ATCC 26403, grown on the yeast extract-peptone-dextrose-fatty acid agar medium (E. Schweizer and H. Bolling, Proc. Nat. Acad. Sci. USA (1970) 67, 660) was suspended in an 0.85% saline solution. One ml portions of this suspension were used to inoculate a 250 ml Erlenmeyer flask (F-1 stage) containing 50 ml of the following medium (YEPD-FA)

| | |
|---|---|
| Sucrose | 20 g |
| Peptone | 20 g |
| Yeast extract | 10 g |
| K$_2$HPO$_4$ | 5 g |
| KH$_2$PO$_4$ | 5 g |
| Myristic acid | 0.07 g |
| Palmitic acid | 0.07 g |
| Stearic acid | 0.07 g |
| Distilled water, q.s. 1 liter | |
| (Sterilized for 15 min at 30 p.s.i.) | |

The flask was incubated at 25° C. on a rotary shaker (250 cycles/min-2" radius) for 24 hours, after which this flask served as the inoculum for a 2000 ml Erlenmeyer flask (F-2 stage) containing 500 ml of the same liquid medium (YEPD-FA). After 20 hours of incubation on a rotary shaker, ethyl-4-chloroacetoacetate (diluted to 3 times its original volume with anhydrous EtOH) was slowly added using a Harvard infusion pump (Model 940) at a rate of 3 ml over a 24 hour period, or 1.2 g of ethyl-4-chloroacetoacetate. After 24 hours, sucrose was then simultaneously infused to the fermentation medium at a rate of 7.1 ml (30% sucrose solution) over 24 hours. The continuous slow addition of substrate was terminated after a total of 4.8 g of ethyl-4-chloroacetoacetate was added (fourth day). However, sucrose was continuously infused into the flask until the fifth day.

(B) Isolation. After 5 days, the content (F-2 stage) was exhaustively extracted with three 400 ml portions of ethyl acetate. The ethyl acetate was dried over Na$_2$SO$_4$ and evaporated to afford 3.6 g of an oily residue. The residue was chromatographed over a silica gel (MN-Kieselgel 60) column. The column was eluted with Skelly B-ethyl acetate (8:1) to yield 1.9 g of ethyl-4-chloro-3(R)-hydroxybutyrate, $[\alpha]_D^{23}$ +20.43° (c, 3.8 CHCl$_3$).

EXAMPLE 370

The procedure of example 369 was repeated using methyl-4-chloroacetoacetate as the substrate to afford methyl-4-chloro-3(R)-hydroxybutyrate, $[\alpha]_D^{23}$ +21.15° (c, 4.2 CHCl$_3$).

EXAMPLE 371

The procedure of example 369 was repeated using t-butyl-4-chloroacetoacetate as the substrate to give t-butyl-4-chloro-3(R)-hydroxybutyrate, $[\alpha]_D^{23}$ +18.09° (c, 5.1 CHCl$_3$).

EXAMPLES 372-374

The procedures of Examples 369–371 were repeated using the mutant, Saccharomyces cerevisiae (ATCC 26405) to obtain optically-active ethyl-4-chloro-3(R)-hydroxybutyrate; methyl-4-chloro-3(R)-hydroxybutyrate, and t-butyl-4-chloro-3(R)-hydroxybutyrate, respectively.

EXAMPLES 375

Methyl-4-chloro-3(R)-hydroxybutyrate (VIII)

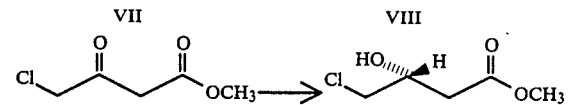

Methyl-4-chloroacetoacetate (VII) (100 mg) was incubated with 29 units of porcine heart (EC 1.1.1.35), B-hydroxyacyl CoA dehydrogenase (Sigma, H4626), and 1.36 g of NADH (Sigma, 90%) in 30 ml of 0.1 M sodium phosphate buffer, pH 6.5.

After 30 hours at 25° C., the reaction mixture was extracted four times with 30 ml of ethyl acetate. The organic layer was dried over sodium sulfate and was evaporated to dryness under reduced pressure. The residue (90 mg) was chromatographed over a silica gel (12 g) column (1.3×34 cm). The column was eluted with a solvent system consisting of Skelly B-ethyl acetate (8:1) and 20 ml fractions were collected. Fractions 9–11 contained the desired methyl-4-chloro-3(R)-hydroxybutyrate (VIII) as revealed by TLC, $[\alpha]^{23}$ +23.5° (c, 5.2 CHCl$_3$) and were pooled.

EXAMPLE 376

The procedure of example 375 was repeated using ethyl-4-chloroacetoacetate as the substrate to afford ethyl-4-chloro-3(R)-hydroxybutyrate, $[\alpha]_D^{23}$ +22.7° (c, 4.7, CHCl$_3$).

EXAMPLE 377

The procedure of example 375 was repeated using n-propyl-4-chloroacetoacetate as the substrate to afford n-propyl-4-chloro-3(R)-hydroxybutyrate, $[\alpha]_D^{23}$ +21.5° (c, 5.0, CHCl$_3$).

EXAMPLE 378

The procedure of example 375 was repeated using n-butyl-4-chloroacetoacetate as the substrate to afford n-butyl-4-chloro-3(R)-hydroxybutyrate, $[\alpha]_D^{23}$ +20.1° (c, 3.1, CHCl$_3$).

General procedure for the conversion of 4-halo-3(R)-hydroxy-butyric esters and amides into L-Carnitine

EXAMPLE 379

A mixture of 4-chloro-3(R)-hydroxybutyric acid octyl ester (1.5 g), ethanol (3 ml) and trimethylamine (25 wt % solution) in water (3 ml) was heated at 80°–90° C. for about 2 hours. The solvents and excess trimethylamine were evaporated to dryness in vacuo to yield 1.8 g of crude residue. The crude product (1 g) was heated at 80°–90° C. in a solution of 10% HCl (7 ml) for 1.5 hours. After evaporation of the solvents under reduced pressure, the crude product was extracted twice with absolute ethanol (10 ml) and the ethanol was evaporated in vacuo. The crystalline residue was dissolved in a small quantity of ethanol and the L-carnitine chloride was precipitated by the addition of ether in good yield (320 mg), m.p. 142° (dec.); [α]- 23.7° (c, 4.5 H$_2$O).

The L-carnitine chloride can be readily converted to the pharmaceutically preferred L-carnitine inner salt by ion exchange means as is well known in the art.

EXAMPLE 380

Octyl-4-iodo-3(R)-hydroxybutyrate (IX)

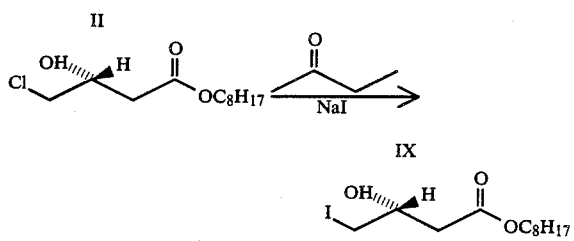

A mixture of octyl-4-chloro-3(R)-hydroxybutyrate (II) (1.426 g), and anhydrous NaI (1.2 g) in 15 ml of methyl ethyl ketone was refluxed for 24 hours. The mixture was rotor evaporated and reacted with ether (100 ml) and water (50 ml). The organic phase was separated and washed with 10% sodium thiosulfate solution (150 ml), brine (150 ml) and dried over anhydrous sodium sulfate. The solvent was evaporated under reduced pressure to afford 1.762 g of IX as a pale-yellow oil; IR (thin film)

3460 cm$^{-1}$ (OH) and 1730 cm$^{-1}$ (ester C=O); PMR (CDCl$_3$), 3.93–4.27 (m, 3H), 3.17 (d, 2H), 2.50 (d, 2H), 1.50–1.87 (m, 2H), 1.30 (bs, 12H), 0.93 (m, 3H).

Transformation of octyl-4-iodo-3(R)-hydroxybutyrate (IX) into L-carnitine

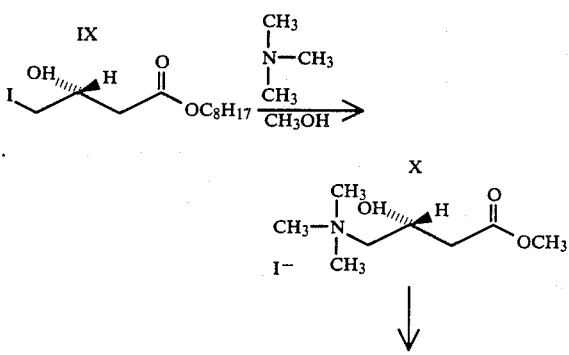

L-Carnitine

To a solution of IX (1.593 g) in methanol (15 ml) was added a 25% solution of aqueous trimethylamine (8 ml). The mixture was stirred at 27° C. for 20 hours. The solvents and the excess trimethylamine were evaporated off under reduced pressure to afford a semi-crystalline solid, X. This residue was washed with small amounts of ether to remove the octanol and then dissolved in water and passed over a Dowex 1-x4 [OH$^-$ form- 50-100 mesh, column volume (2.5×15 cm). The column was washed with distilled water. Removal of the solvent in vacuo from the first 200 ml of the eluate gave L-carnitine as a white crystalline solid (490 mg, 65% yield) [α]$_D^{23}$ 29.2° (c, 6.5 H$_2$O).

EXAMPLE 381

The procedure of example 380 was repeated using hexyl-4-chloro-3(R)-hydroxybutyrate to yield hexyl-4-iodo-3(R)-hydroxybutyrate, which was then converted to L-carnitine.

EXAMPLE 382

The procedure of example 380 was repeated using heptyl-4-chloro-3(R)-hydroxybutyrate to yield heptyl-4--iodo-3(R)-hydroxybutyrate, which was then converted to L-carnitine.

EXAMPLE 383

The procedure of example 380 was repeated using decyl-4-chloro-3(R)-hydroxybutyrate to yield decyl-4-iodo-3(R)-hydroxybutyrate, which was then converted to L-carnitine.

EXAMPLE 384

The procedure of example 380 was repeated using methyl-4-chloro-3(R)-hydroxybutyrate (VIII) to give methyl-4-iodo-3(R)-hydroxybutyrate, which was then converted into L-carnitine.

EXAMPLE 385

The procedure of example 380 was repeated using ethyl-4-chloro-3(R)-hydroxybutyrate to give ethyl-4-iodo-3(R)-hydroxybutyrate, which was then converted into L-carnitine.

EXAMPLE 386

The procedure of example 380 was repeated using n-propyl-4-chloro-3(R)-hydroxybutyrate to give n-propyl-4-iodo-3(R)-hydroxybutyrate, which was then converted into L-carnitine.

EXAMPLE 387

The procedure of example 380 was repeated using n-butyl-4-chloro-3(R)-hydroxybutyrate to give n-butyl-4-iodo-3(R)-hydroxybutyrate, which was then converted into L-carnitine.

EXAMPLE 388

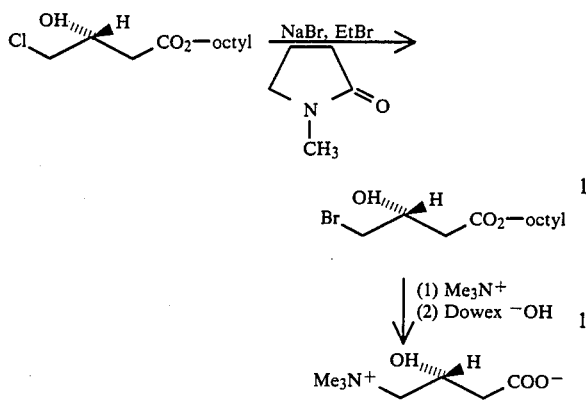

To a solution of (R)-(+)-octyl-4-chloro-3-hydroxybutyrate (1.5 g, ee 81.4%) in N-methylpyrrolidinone (11 ml), in a 100 ml RB flask fitted with an efficient condensor, was added sodium bromide (140 mg) and ethyl bromide (3 ml). The mixture was heated at 60°–70° C. under a dry atmosphere for 48 hours and then worked up by dilution with water and extraction twice with ether. An nmr spectrum of the product showed substantial amounts of residual chloride. The product was redissolved in N-methylpyrrolidinone (11 ml) and charged with sodium bromide (0.2 g) and ethyl bromide (3 ml). The mixture was heated at 60°–70° C. as before for nearly five days. The mixture was diluted with water and extracted twice with ether. On drying ($Na_2SO_4$) and subsequent removal of the solvent, the bromide was obtained as a pale yellow oil (1.694 g, 95.4% yield), of sufficient purity to be directly used in the next step.

The crude (R)-(+)-octyl-4-bromo-3-hydroxybutyrate (756 mg) in methanol (10 ml) in a 100 ml RB flask was charged with a 25% aqueous solution of trimethylamine (5 ml). The flask was stoppered and the mixture stirred at room temperature for nearly 4 ½ days. The solvents were removed by rotor evaporator and the residue pumped for a short time. The viscous oil was triturated a few times with small amounts of ether. The residual gum was dissolvewd in a small amount of water and passed through a Dowex-1-X-4 $^{-}OH$ column (length 7 cm, width 2 cm). The column was eluted with distilled water (150 ml). Rotor evaporation of the water and subsequent azeotropic drying with isobutyl alcohol gave L-carnitine as a white crystalline solid [216 mg, corresponds to overall yield of 50.1% from (R)-(+)-octyl-4-chloro-3-hydroxybutyrate.

Representative yeasts that produce the desired enzyme are listed in Tabl⑧1 and representative fungi are listed in Table 2.

TABLE 1

(Yeasts)

1. *Candida lipolytica* NRRL Y-1095
2. *Candida pseudotropicalis* NRRL Y-1264
3. *Mycoderma cerevisiae* NRRL Y-1615
4. *Torula lactosa* NRRL Y-329
5. *Geotrichum candidum* NRRL Y-552
6. *Hansenula anomala* NRRL Y-366
7. *Hansenula subpelliculosa* NRRL Y-1683
8. *Pichia alcoholophila* NRRL Y-2026
9. *Saccharomyces cerevisiae* NRRL Y-12, 632
10. *Saccharomyces lactis* NRRL Y-1140
11. *Zygosaccharomyces priorianus* NRRL Y-12,624

TABLE 1-continued (Yeasts)

12. *Saccharomyces acidifaciens* NRRL Y-7253
13. *Kloeckera corticis* ATCC 20109
14. *Cryptococus mascerans* ATCC 24194
15. *Rhodotorula sp.* ATCC 20254
16. *Candida albicans* ATCC 752
17. *Dipodascus albidus* ATCC 12934
18. *Saccharomyces cerevisiae* (commercial Red Star)
19. *Rhodotorula rubra* NRRL Y-1592
20. *Oospora lactis* ATCC 14318
21. *Saccharomyces cerevisiae* ATCC 26403
22. *Saccharomyces cerevisiae* ATCC 26405

NRRL - Northern Regional Research Lab at Peoria, Illinois
ATCC - American Type Culture Collection at Rockville, Maryland.

TABLE 2

(Fungi)

1. *Gliocladium virens* ATCC 13362
2. *Caldariomyces fumago* ATCC 16373
3. *Linderina pennisopora* ATCC 12442
4. *Aspergillus ochraceus* NRRL 405
5. *Trichoderma lignorum* ATCC 8678
6. *Heterocephalum autantiacum* ATCC 16328
7. *Entomophthora coronata* NRRL 1912
8. *Scopulariopsis constantini* NRRL 1860
9. *Zygorhynchus heterogamus* ATCC 6743
10. *Scopulariopsis brevicaulis* NRRL 2157
11. *Rhizopus arrhizus* NRRL 2286
12. *Penicillium thomii* NRRL 2077
13. *Mucor hiemalis* (−) NRRL 4088
14. *Byssochlamys nivea* ATCC 12550
15. *Penicillium patulum* NRRL 1952
16. *Metarrhizium anisopliae* ATCC 24942
17. *Penicillium islandicum* ATCC 10127
18. *Cunninghamella elegans* ATCC 10028a
19. *Cunninghamella echinulata* ATCC 11585a
20. *Aspergillus fumigatus* ATCC 16907
21. *Aspergillus amstelodami* NRRL 90
22. *Gliocladium roseum* ATCC 10521
23. *Aspergillus giganteus* ATCC 10059
24. *Absidia blakeleeana* ATCC 10148b
25. *Penicillium roqueforti* NRRL 849a

EXAMPLE 389

The procedure of example 388 was repeated using methyl-4-chloro-3(R)-hydroxybutyrate to give methyl-4-bromo-3(R)-hydroxybutyrate, which was then converted into L-carnitine.

EXAMPLE 390

The procedure of example 388 was repeated using ethyl-4-chloro-3(R)-hydroxybutyrate to give ethyl-4-bromo-3(R)-hydroxybutyrate, which was then converted into L-carnitine.

EXAMPLE 391

The procedure of example 388 was repeated using propyl-4-chloro-3(R)-hydroxybutyrate to give propyl-4-bromo-3(R)-hydroxybutyrate, which was then converted into L-carnitine.

EXAMPLE 392

The procedure of example 388 was repeated using t-butyl-4-chloro-3(R)-hydroxybutyrate to give t-butyl-4-bromo-3(R)-hydroxybutyrate, which was then converted into L-carnitine.

What is claimed is:
1. A process for preparing optically active 4-substituted 3(R) hydroxybutyric acid derivatives having the formula and 3(R) configuration

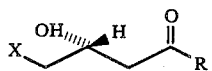

wherein X is Cl,; and R is an alkoxy radical having from 1 to 4 carbon atoms which comprises subjecting compounds having the formula

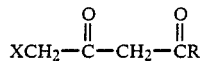

wherein X and R have the above-identified meaning to the enzymatic action of an oxido-reductase (EC 1.1.1.35), and recovering the thus formed optically active 4-substituted 3(R)-hydroxybutyric acid derivatives from the enyzmatic reaction mixture.

2. The process of claim 1, wherein said oxido-reductase (EC 1.1.1.35) is a purified form that is isolated from porcine heart.

3. The process of claim 1, wherein said oxido-reductase is supplied by a microorganism that lacks the β-keto reductase component of fatty acid synthetase.

* * * * *